United States Patent [19]
Tachibana et al.

[11] Patent Number: 5,660,909

[45] Date of Patent: *Aug. 26, 1997

[54] SHEET FOR MEASURING ULTRASONIC WAVES

[75] Inventors: Katsuro Tachibana; Shunro Tachibana, both of Fukuoka-ken, Japan

[73] Assignee: Ekos Corporation, Bothell, Wash.

[ * ] Notice: The term of this patent shall not extend beyond the expiration date of Pat. No. 5,440,914.

[21] Appl. No.: 530,671

[22] Filed: Sep. 19, 1995

[30] Foreign Application Priority Data

Sep. 22, 1994 [JP] Japan ................... 6-228373

[51] Int. Cl.$^6$ .................. B32B 3/02; G01N 29/00
[52] U.S. Cl. ................ 428/76; 73/649; 181/139; 367/13; 428/68; 428/69; 428/320.2; 428/321.1; 428/323

[58] Field of Search .................. 428/76, 68, 69, 428/323, 320.2, 321.1; 73/1 DV, 649; 367/13; 181/139

[56] References Cited

U.S. PATENT DOCUMENTS

| | | |
|---|---|---|
| 5,342,608 | 8/1994 | Moriya ........................ 424/9 |
| 5,440,914 | 8/1995 | Tachibana ................. 73/1 DV |

*Primary Examiner*—Nasser Ahmad
*Attorney, Agent, or Firm*—Wilson Sonsini Goodrich & Rosati

[57] ABSTRACT

A sheet for measuring ultrasonic waves with which it is possible to easily measure a 2-dimensional ultrasonic wave distribution comprises a fluid in which multiple bubbles, each consisting of a minute quantity of gas covered by an extremely thin covering, are dispersed and sealed in a transparent baglike sheet.

4 Claims, 4 Drawing Sheets

5,660,909

SHEET FOR MEASURING ULTRASONIC WAVES

BACKGROUND OF THE INVENTION

1. Field of the Invention

This invention relates to a sheet for measuring ultrasonic waves, which can be used for measuring the ultrasonic wave strength distribution of ultrasound used in ultrasonic medical diagnostic equipment, ultrasonic medical treatment equipment and the like.

2. Prior Art

It is important to know the sound field distribution and strength of ultrasound emitted by, for example, an ultrasonic medical diagnostic apparatus to clearly see the effects of ultrasound on the body and to evaluate the performance and safety of the ultrasonic medical diagnostic apparatus.

Furthermore, with an ultrasonic treatment apparatus, it is necessary to beam concentrated ultrasonic waves at a diseased area, and so it is also necessary to check what kind of irradiation characteristics the oscillating device used for treatment has. Furthermore, even if desired characteristics are obtained at a specific frequency, there is a possibility that at other frequencies the characteristics will be different, and so it is necessary to ascertain the characteristics at various frequencies.

Various methods for measuring the strength and strength distribution of ultrasonic waves have been known.

For example, by disposing an ultrasonic microphone in a liquid being irradiated with ultrasonic waves, the strength of the ultrasonic waves in the position in which the ultrasonic microphone is disposed is measured. Also, by changing the position of the ultrasonic microphone, it is possible to measure the strength distribution of the ultrasonic waves.

However, there are the following problems with the measuring method using an ultrasonic microphone: (1) Because an ultrasonic microphone having a certain volume is disposed in a liquid, the ultrasonic wave distribution is disturbed by the presence of the ultrasonic microphone itself, making accurate strength distribution measurement impossible. (2) Because the frequency band of an ultrasonic microphone is generally small, it is not possible to measure the strength distribution of ultrasound extending over a wide frequency range. (3) Because ultrasonic microphones generally have specific directional characteristics, measurement results vary depending on the attitude in which the ultrasonic microphone is disposed. (4) The characteristics of an ultrasonic oscillating device cannot be ascertained intuitively from measured numerical data, and it is necessary to plot the data on a graph or otherwise process it. (5) To measure an ultrasonic wave distribution in real time it is necessary to deploy multiple ultrasonic microphones, but since ultrasonic microphones are very expensive it is difficult to provide a large number of them.

In addition to the measuring method using an ultrasonic microphone as described above, there are also optical methods such as the Schlieren method wherein fluctuation in refractive index caused by ultrasonic wave irradiation is detected optically. With this optical method, it is possible to make visible and to measure sound field strength distribution without the measuring equipment itself disrupting the state of the sound field being measured. However, the optical method has the problem of requiring an image-forming optical system, including a special light source, lenses and the like. Furthermore, the measuring apparatus is quite large.

Also known is a method of utilizing an acoustic luminescence phenomenon wherein certain substances become luminous slightly when they are irradiated with ultrasonic waves, and the 3-dimensional distribution of ultrasonic waves is measured by extended-exposure photography. However, because this method does not allow direct viewing, one must carry out the photography and developing before viewing the results. This all takes a lot of time.

Accordingly, an object of this invention is to provide a sheet for measuring ultrasonic waves with which it is possible to easily measure a 2-dimensional ultrasonic wave distribution.

SUMMARY OF THE INVENTION

To achieve the above-mentioned object, this invention provides a sheet for measuring ultrasonic waves comprising a fluid in which multiple bubbles, each consisting of a minute quantity of a gas covered by an extremely thin covering, are dispersed and sealed in a transparent baglike sheet.

When so many bubbles covered by very thin coverings made of protein or the like are dispersed in a fluid contained in a transparent baglike sheet, optical reflections on the surfaces of the bubbles make the fluid look milky. When ultrasonic waves are directed at this bubble-containing fluid, their energy induces cavitation in the bubbles, causing the bubbles to burst and the gas inside the bubbles to dissolve in the fluid. As a result, there ceases to be any reflection at the surfaces of the bubbles and the regions in the fluid where the bubbles burst become transparent. Therefore, the regions where the fluid become transparent show the irradiation pattern of the ultrasonic waves. Also, the degree of transparency shows the strength of the ultrasonic waves.

DETAILED DESCRIPTION OF THE PREFERRED EMBODIMENTS

The invention will now be described specifically based on the preferred embodiments thereof with reference to the accompanying drawings.

Figure 1A:
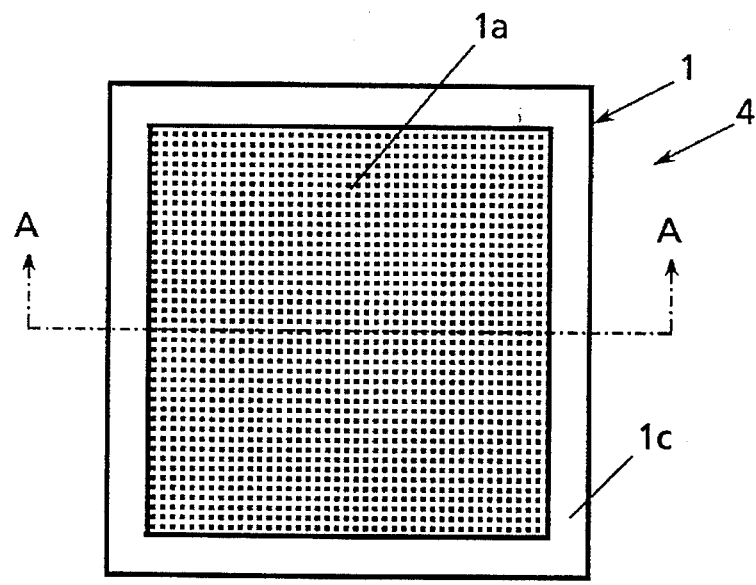
FIG. 1A is a plan view of a preferred embodiment of a sheet for measuring ultrasonic waves according to the invention and FIG. 1B is a sectional view along the line A—A in FIG. 1A.
Figure 1B:
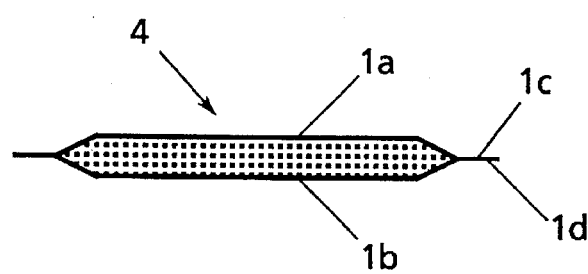
Figure 2:
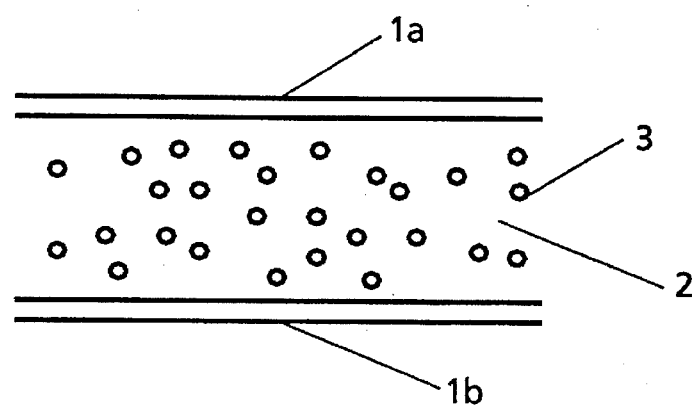
FIG. 2 is a view schematically illustrating bubbles dispersed in a fluid.

FIG. 1A is a plan view of an example of a sheet for measuring ultrasonic waves according to the invention and FIG. 1B is a sectional view along the line A—A in FIG. 1A. FIG. 2 is a view schematically illustrating bubbles dispersed in a fluid.

A pair of rectangular, transparent sheets 1a, 1b made of an elastic synthetic resin such as polyethylene are disposed one on top of the other, with edge portions 1c, 1d of the transparent sheets 1a, 1b being adhered together by thermal welding, ultrasonic waves, or the like to form a sealed baglike sheet 1. The size of the baglike sheet 1 may be about several cm×several cm.

As shown in FIG. 2, the inside of the baglike sheet 1 is filled with a fluid 2 such as a sol or a gel, and numerous bubbles 3, each consisting of a minute quantity of gas covered by an extremely thin film made of a protein or the like are dispersed substantially and uniformly in the fluid 2. The thickness of the baglike sheet 1 when it has been filled with the fluid 2 containing the bubbles 3 may be 0.1 mm to several mm. In this preferred embodiment, this baglike sheet 1 filled with the fluid 2 containing the bubbles 3 will be called a sheet for measuring ultrasonic waves 4.

As the bubbles 3, Albunex (trademark) made by MBI Co. of the U.S. can be used. These bubbles 3 are dispersed in the fluid 2 at a concentration of, for example, about 50 to 400 million bubbles per cc. The diameter of the bubbles 3 is 5–50 µm. The concentration and diameter of the bubbles 3 are set at values that, as will be later explained, will cause fluid 2 to become visibly transparent when bubbles 3 are irradiated with ultrasonic waves and burst. In FIG. 2, for simplicity of illustration, the bubbles 3 are shown as numerous separate circles, but because the bubbles 3 are extremely small in diameter and extremely great in number, the whole actually looks like a milky liquid.

Figure 3A:
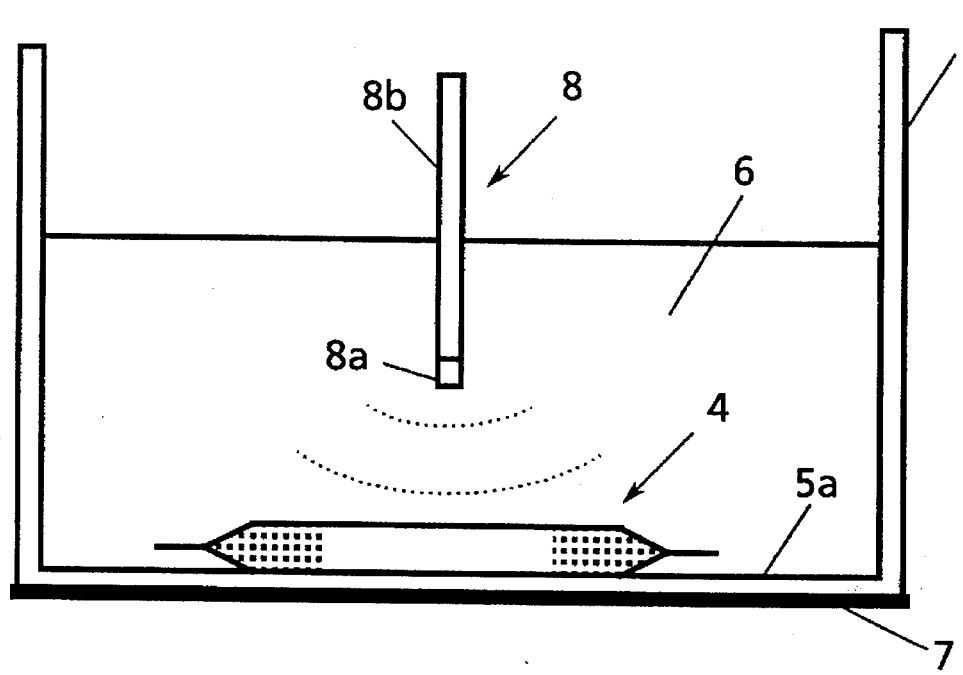
FIGS. 3A and 3B are views illustrating a way of using a sheet for measuring ultrasonic waves according to the invention.

FIG. 3 is a view illustrating a way of using the sheet for measuring ultrasonic waves 4 of this preferred embodiment.

The sheet for measuring ultrasonic waves 4 is placed horizontally on the bottom 5a of a water tank 5, and the water tank 5 is filled with an ultrasonic wave transmitting medium 6 such as a liquid or a gel. A background plate 7 of a relatively dark color such as dark blue or black with uniform density is disposed underneath the bottom 5a of the water tank 5.

An ultrasonic wave generating device 8, for which irradiation characteristics are to be measured, is disposed in the ultrasonic wave transmitting medium 6 in the water tank 5. This ultrasonic wave generating device 8 comprises an ultrasonic oscillator device 8a and a barlike supporting member 8b on which this ultrasonic oscillator device 8a is mounted.

When no ultrasonic wave signal is being supplied to the ultrasonic oscillator device 8a, fluid 2 in the sheet for measuring ultrasonic waves 4 is viewed from above as uniformly milky. This is because light is reflected by the surfaces of the many bubbles 3 contained in the fluid 2 and enters the eyes of the viewer. Although the dark background plate 7 is disposed behind the sheet for measuring ultrasonic waves 4, because the many bubbles 3 block the light path between the eyes of the viewer and the background plate 7, the background plate 7 cannot be seen directly. Even if it is seen it only appears as a very faint color.

Figure 3B:
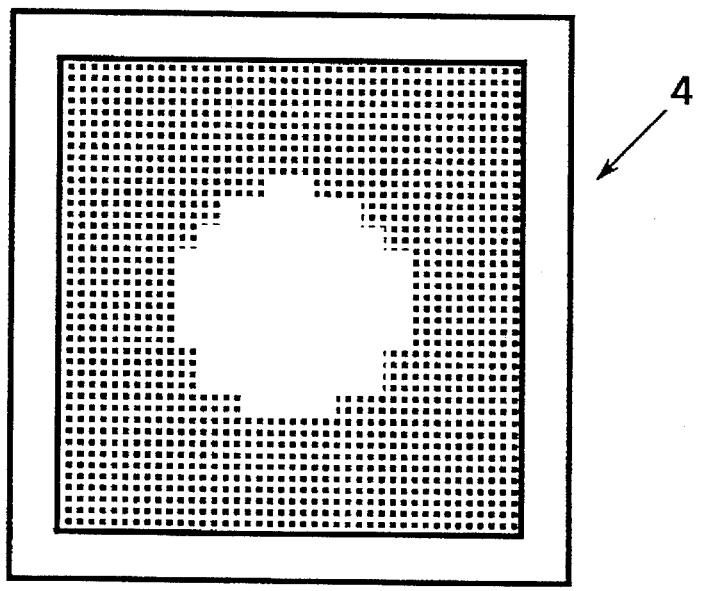

When an ultrasonic signal is then supplied to the ultrasonic oscillator device 8a, ultrasonic waves are transmitted by the ultrasonic wave transmitting medium 6 and irradiated into the fluid 2, the energy of the ultrasonic waves induces cavitation in the bubbles 3 in the fluid 2, causing the bubbles 3 to burst and the gas inside the bubbles 3 to dissolve in the fluid 2. As a result there ceases to be reflections by the surfaces of the bubbles 3 and, as shown in FIG. 3B, the regions of the fluid 2 where the bubbles 3 have burst become transparent. Thus, the regions of the fluid 2 which have become transparent show the irradiation pattern of the ultrasonic waves. Also, the stronger the irradiation of a region the more transparent that region becomes. In FIG. 3, the black points schematically show bubbles and the white areas schematically show a transparent pattern. The coverings of the bubbles 3 which have burst are very small and therefore do not affect the light reflection.

Here, because the dark background plate 7 is disposed behind the sheet for measuring ultrasonic waves 4, when the sheet for measuring ultrasonic waves 4 is viewed from above the color of the background plate 7, for example dark blue, is visible where the fluid 2 has become transparent. That is, because the transparent pattern can be seen as a blue pattern, it is very easy to see.

When a gel is used as the fluid 2, because the gel-fluid 2 hardly moves, the irradiation pattern formed remains as it is and can be viewed even after a long time after the event.

Figure 4:
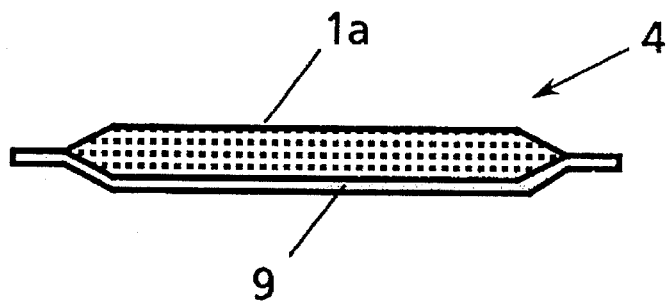
FIG. 4 is an outline sectional view of another preferred embodiment of a sheet for measuring ultrasonic waves according to the invention.

FIG. 4 is an outline sectional view of another preferred embodiment of a sheet for measuring ultrasonic waves according to the invention. In the preferred embodiment shown in FIG. 4, adhesive tape 9 is affixed to one side, for example to transparent sheet 1b, of the sheet for measuring ultrasonic waves 4. A protective sheet (not shown in the drawings) which can be peeled of is affixed to the surface of the adhesive tape 9. The sheet for measuring ultrasonic waves 4 having this adhesive tape 9 affixed thereto is used to measure the strength of ultrasonic waves directed into body tissue during ultrasonic wave diagnosis or ultrasonic wave treatment.

When the sheet for measuring ultrasonic waves 4 shown in FIG. 4 is used, the protective sheet (not shown in the drawings) is first peeled off the surface of the adhesive tape 9 and affixed to the skin in an afflicted area or an area to be diagnosed on a patient. Then an ultrasonic wave generating device is pressed against the skin by way of the sheet for measuring ultrasonic waves 4, and ultrasonic wave application is commenced. As described above, the state of bursting the bubbles 3 in the fluid 2 of the sheet for measuring ultrasonic waves 4 changes according to the strength of the ultrasonic waves, and therefore, by measuring the relationship between the ultrasonic wave strength and the state of bursting the bubbles 3 in advance it is possible to deduce the strength of ultrasonic waves from the state of bursting the bubbles 3. Therefore, it is possible to adjust the strength of the ultrasonic waves applied to the patient to a suitable level. Also, because it is possible to know the irradiation pattern of the ultrasonic waves, the ultrasonic waves can be applied in the correct locations.

Figure 5:
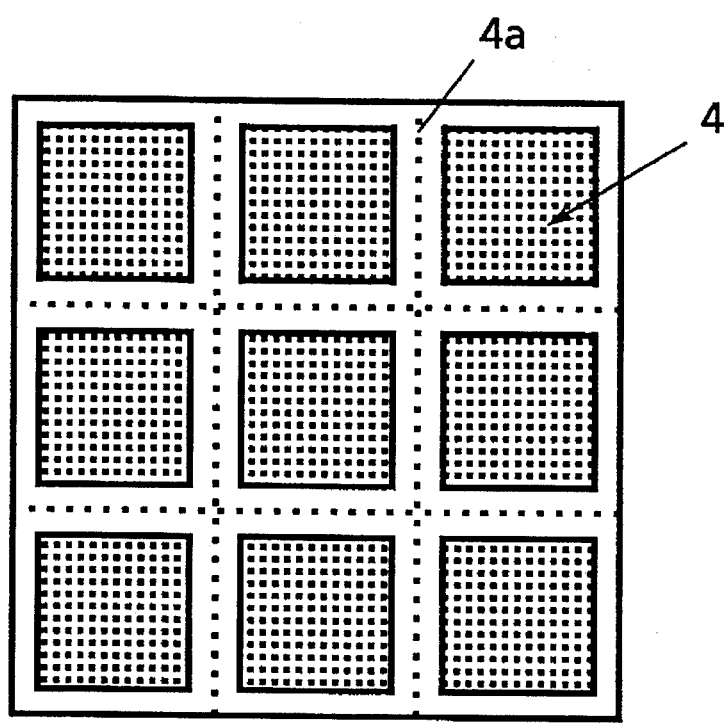
FIG. 5 is an outline sectional view of a further preferred embodiment of a sheet for measuring ultrasonic waves according to the invention.

FIG. 5 is a plan view of a further preferred embodiment of a sheet for measuring ultrasonic waves according to the invention. In the preferred embodiment shown in FIG. 5, multiple sheets for measuring ultrasonic waves 4 are formed continuously, and perforated lines 4a are provided at the boundaries of the sheets for measuring ultrasonic waves 4. When investigating the irradiation pattern of ultrasonic waves extending over a relatively wide area, multiple sheets for measuring ultrasonic waves 4 can be used in their connected state, and when investigating the irradiation pattern of ultrasonic waves extending over a relatively narrow area, multiple sheets for measuring ultrasonic waves 4 can be torn off at the perforated lines 4a and used individually. In the preferred embodiment shown in FIG. 5 also, adhesive tape may be provided on one surface of the sheets for measuring ultrasonic waves 4 as in the preferred embodiment shown in FIG. 4.

Figure 6:
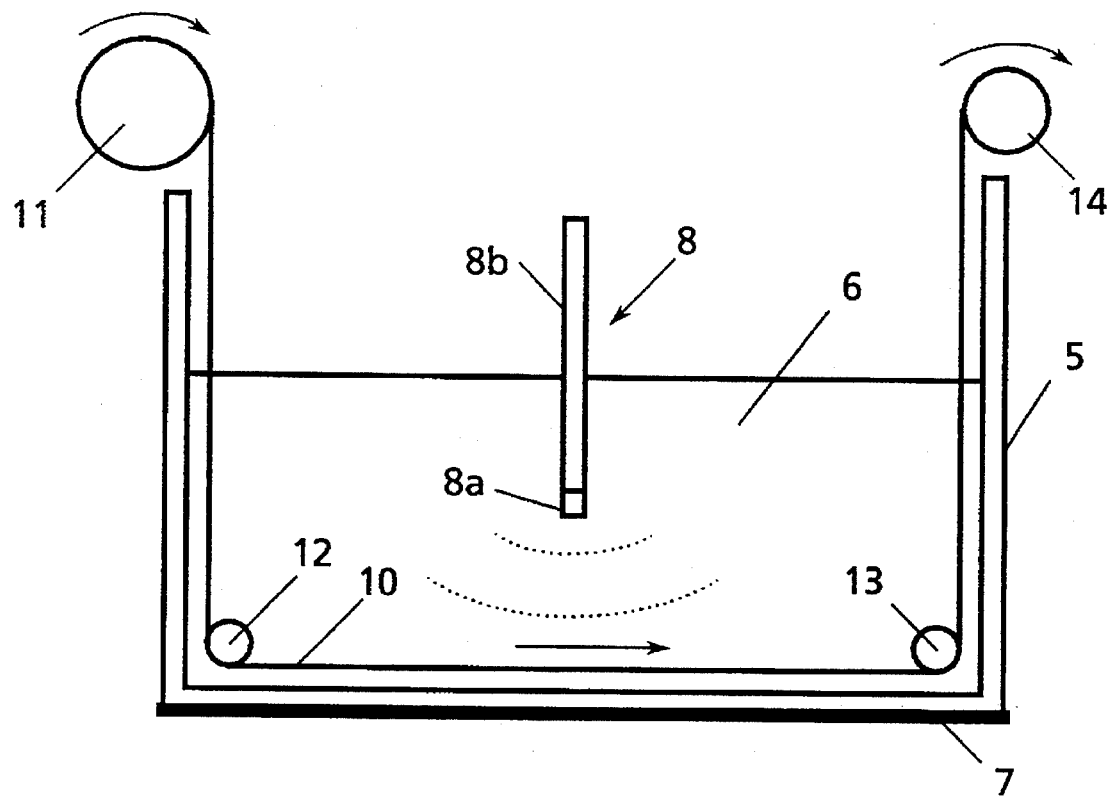
FIG. 6 is an outline sectional view illustrating another way of using a sheet for measuring ultrasonic waves according to the invention.
Figure 7:
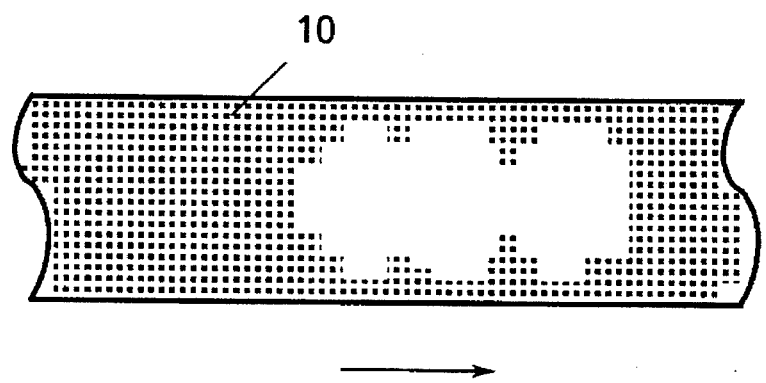
FIG. 7 is a view illustrating an example of measurement of ultrasonic wave strength.

FIG. 6 is an outline sectional view showing another way of using a sheet for measuring ultrasonic waves according to the invention. In the preferred embodiment shown in FIG. 6, a sheet for measuring ultrasonic waves is in tape form, and this tape-form sheet for measuring ultrasonic waves 10 is fed out from a feedout reel 11, guided along the bottom of a water tank 5 by guide rollers 12 and 13, and taken up by a takeup roller 14. By controlling the generation of ultrasonic waves from an ultrasonic wave generating device 8 while the tape-form sheet for measuring ultrasonic waves 10 is continuously moved, as shown in FIG. 7, changes in the ultrasonic wave strength can be observed continuously.

The preferred embodiments described above were described using the example of ultrasonic medical diagnosis or ultrasonic medical treatment; however, the invention is not limited to this application, and a sheet for measuring ultrasonic waves according to the invention can be applied to anything which might be irradiated with ultrasonic waves. For example, by affixing sheets for measuring ultrasonic waves according to the invention to parts of a motor vehicle, because ultrasonic energy generated during contact and collisions bursts the bubbles, by investigating the relationship between the impact and the bursting states of the bubbles in advance it would be possible to deduce what amounts of force are being applied and where. In other words, recording of one-off phenomena is possible.

Also, by altering the size of the bubbles and the thickness of the film, sheets for measuring ultrasonic waves of specific ultrasonic wave strengths and frequencies can be made.

Also, although in the preferred embodiments described above, ultrasonic waves were irradiated in a direction perpendicular to the surface of the sheet for measuring ultrasonic waves, the ultrasonic waves may alternatively be irradiated in a direction parallel to the surface of the sheet for measuring ultrasonic waves.

Because, as described above, in this invention a fluid containing bubbles which are burst by ultrasonic waves is sealed in a baglike sheet, the bubbles are burst by ultrasonic waves, and the strength of the ultrasonic waves can be observed by the degree of transparency of the fluid, the following effects are obtained:

(1) The characteristics of an ultrasonic oscillator device can be measured at low cost.

(2) The characteristics of an ultrasonic oscillator device can be measured 2-dimensionally.

(3) The characteristics of an ultrasonic oscillator device can be measured in real time.

(4) The characteristics of an ultrasonic oscillator device can be ascertained intuitively in a short time.

(5) Because the energy of the ultrasonic waves is not consumed, they can be measured while actually being used for diagnosis or treatment.

(6) It is possible to measure an irradiation pattern of ultrasonic wave energy in detail.

What is claimed is:

1. An ultrasonic wave measuring sheet comprising a fluid in which multiple bubbles each consisting of a minute quantity of gas covered by a covering sufficiently thin to burst upon exposure to a level of ultrasonic wave energy are dispersed and sealed in a transparent sealed disclosure sheet.

2. An ultrasonic wave measuring sheet according to claim 1, wherein so many bubbles covered by coverings that are sufficiently thin to burst up on exposure to a level of ultrasonic wave energy and made of protein are dispersed in a fluid or gel contained in said sealed enclosure sheet.

3. An ultrasonic wave measuring sheet according to claim 2, wherein said bubbles are dispersed in the fluid at a concentration of about 50 to 400 million bubbles per cc.

4. An ultrasonic wave measuring sheet according to claim 2, wherein the diameter of each of said bubble is 5–50 μm.

* * * * *

UNITED STATES PATENT AND TRADEMARK OFFICE
CERTIFICATE OF CORRECTION

PATENT NO. : 5,660,909  
DATED : August 26, 1997  
INVENTOR(S) : Katsuro Tachibana and Shunro Tachibana It is certified that error appears in the above-identified patent and that said Letters Patent is hereby corrected as shown below:

<u>Title page,</u>  
Item [73], Assignee, delete "Ekos Corporation, Bothell, WA (US)"

Signed and Sealed this

First Day of June, 2004

JON W. DUDAS  
*Acting Director of the United States Patent and Trademark Office*